US010692211B2

United States Patent
Madabhushi et al.

(10) Patent No.: US 10,692,211 B2
(45) Date of Patent: Jun. 23, 2020

(54) INTRA-PERINODULAR TEXTURAL TRANSITION (IPRIS): A THREE DIMENISONAL (3D) DESCRIPTOR FOR NODULE DIAGNOSIS ON LUNG COMPUTED TOMOGRAPHY (CT) IMAGES

(71) Applicant: Case Western Reserve University, Cleveland, OH (US)

(72) Inventors: Anant Madabhushi, Shaker Heights, OH (US); Mehdi Alilou, Cleveland, OH (US)

(73) Assignee: Case Western Reserve University, Cleveland, OH (US)

( * ) Notice: Subject to any disclaimer, the term of this patent is extended or adjusted under 35 U.S.C. 154(b) by 90 days.

(21) Appl. No.: 16/012,937

(22) Filed: Jun. 20, 2018

(65) Prior Publication Data

US 2018/0365829 A1   Dec. 20, 2018

Related U.S. Application Data

(60) Provisional application No. 62/522,231, filed on Jun. 20, 2017.

(51) Int. Cl.
*G06T 7/00* (2017.01)
*G06K 9/62* (2006.01)
(Continued)

(52) U.S. Cl.
CPC .......... *G06T 7/0012* (2013.01); *G06K 9/6261* (2013.01); *G06K 9/6269* (2013.01);
(Continued)

(58) Field of Classification Search
CPC ....... G06T 7/0012; G06T 7/187; G06T 7/194; G06T 7/11; G06T 7/174; G06T 7/40; G06T 15/08; G06T 2207/10081; G06T 2207/10104; G06T 2207/20076; G06T 2207/20081; G06T 2207/20084;
(Continued)

(56) References Cited

U.S. PATENT DOCUMENTS

2011/0311124 A1\* 12/2011 Ohnishi ................ G06T 7/0012
382/134
2016/0196648 A1\* 7/2016 Madabhushi ...... C07K 16/2803
382/131

(Continued)

*Primary Examiner* — Pakee Fang
(74) *Attorney, Agent, or Firm* — Eschweiler & Potashnik, LLC

(57) ABSTRACT

Embodiments classify lung nodules by accessing a 3D radiological image of a region of tissue, the 3D image including a plurality of voxels and slices, a slice having a thickness; segmenting the nodule represented in the 3D image across contiguous slices, the nodule having a 3D volume and 3D interface, where the 3D interface includes an interface voxel; partitioning the 3D interface into a plurality of nested shells, a nested shell including a plurality of 2D slices, a 2D slice including a boundary pixel; extracting a set of intra-perinodular textural transition (Ipris) features from the 2D slices based on a normal of a boundary pixel of the 2D slices; providing the Ipris features to a machine learning classifier which computes a probability that the nodule is malignant, based, at least in part, on the set of Ipris features; and generating a classification of the nodule based on the probability.

18 Claims, 9 Drawing Sheets

(51) Int. Cl.
    *G06T 7/40*     (2017.01)
    *G06T 7/174*     (2017.01)
    *G16H 30/20*     (2018.01)
    *G06T 15/08*     (2011.01)
    *G06T 7/11*     (2017.01)
    *G06T 7/187*     (2017.01)
    *G06T 7/194*     (2017.01)
    *G16H 20/40*     (2018.01)
    *G16H 30/40*     (2018.01)
    *G16H 50/20*     (2018.01)
    *G16H 20/17*     (2018.01)

(52) U.S. Cl.
    CPC ................ *G06T 7/11* (2017.01); *G06T 7/174* (2017.01); *G06T 7/187* (2017.01); *G06T 7/194* (2017.01); *G06T 7/40* (2013.01); *G06T 15/08* (2013.01); *G16H 30/20* (2018.01); *G06K 2209/053* (2013.01); *G06T 2207/10081* (2013.01); *G06T 2207/10104* (2013.01); *G06T 2207/20076* (2013.01); *G06T 2207/20081* (2013.01); *G06T 2207/20084* (2013.01); *G06T 2207/20152* (2013.01); *G06T 2207/30064* (2013.01); *G06T 2207/30096* (2013.01); *G16H 20/17* (2018.01); *G16H 20/40* (2018.01); *G16H 30/40* (2018.01); *G16H 50/20* (2018.01)

(58) Field of Classification Search
    CPC . G06T 2207/20152; G06T 2207/30064; G06T 2207/30096; G16H 30/20; G16H 20/17; G16H 20/40; G16H 50/20; G16H 30/40; G06K 9/6261; G06K 9/6269; G06K 2209/053
    See application file for complete search history.

(56) References Cited

U.S. PATENT DOCUMENTS

| | | | |
|---|---|---|---|
| 2017/0140533 A1* | 5/2017 | Nelson | G01N 15/1468 |
| 2018/0012356 A1* | 1/2018 | Madabhushi | G06T 7/0014 |
| 2019/0213736 A1* | 7/2019 | Varekamp | G06T 7/12 |

\* cited by examiner

INTRA-PERINODULAR TEXTURAL TRANSITION (IPRIS): A THREE DIMENISONAL (3D) DESCRIPTOR FOR NODULE DIAGNOSIS ON LUNG COMPUTED TOMOGRAPHY (CT) IMAGES

CROSS REFERENCE TO RELATED APPLICATIONS

This application claims the benefit of U.S. Provisional Application 62/522,231, filed Jun. 20, 2017, which is incorporated herein in its entirety.

FEDERAL FUNDING NOTICE

This invention was made with government support under grants 1U24CA199374-01, R01CA202752-01A1, R01CA208236-01A1, R21CA179327-01, R21CA195152-01, R01DK098503-02, and 1 C06 RR012463-01 awarded by the National Institutes of Health. Also grants W81XWH-13-1-0418, W81XWH-14-1-0323, W81XWH16-1-0329, and W81XWH-15-1-0613 awarded by the Department of Defense. The government has certain rights in the invention.

BACKGROUND

Characterizing lung nodules on computed tomography (CT) images is a challenging clinical task. Granulomas, which are benign presentations but appear as malignant nodules on chest CT scans, are considered among the most difficult tumor confounders to discern. Adenocarcinomas are malignant lesions or nodules. Granulomas and adenocarcinomas are often indistinguishable on both CT and positron emission tomography (PET) scans. For example, both types of nodules appear "hot" on PET imagery. Hence, many people with benign nodules are subjected to unnecessary surgical procedures due to the inability to make confident diagnostic predictions with respect to the nodule on CT. Consequently there is a need for discriminating radiomic features for improved characterization of lung nodules on CT scans.

Existing approaches for distinguishing adenocarcinoma from granuloma employ textural, intensity, or shape analysis for radiomic characterization of lung nodules. For example, shape features (e.g., surface area, volume, and surface to volume ratio), together with textural and intensity features extracted from CT data of lung and oropharyngeal cancers, may be associated, using unsupervised clustering, with underlying gene-expression profiles of lung cancer patients. Existing approaches may employ automated three dimensional (3D) active contour segmentation to segment nodules and then extract morphological and textural features from the segmented nodules. One existing approach analyzed with a leave-one out cross validation yielded an AUC of 0.83 in a data set of 44 malignant and 52 benign nodules. Another existing approach achieved AUC values between 0.68 and 0.92 with 48 malignant and 33 benign nodules. One common attribute associated with the majority of these existing radiomic related approaches for lung nodule characterization is that they involve features pertaining to the nodule alone. Furthermore, these existing texture-based features tend to be affected by the choice of scanner, reconstruction kernel, and slice thickness.

Lymphocytic infiltration is associated with malignant lung nodules. The infiltration appears within the perinodular space of malignant nodules, which in turn causes differential textural patterns adjacent to the nodule. However, lymphocytic infiltration does not typically co-occur with granulomas and benign nodules. Some attempts have been proposed towards this end through the concept of margin sharpness. One existing version of the margin sharpness descriptor approach calculates the sharpness of the intensity transition across the lesion. However, existing margin sharpness approaches limit the interrogation of intensity changes to the nodule interface. Existing approaches ignore the whole core of the tumor. Thus, existing approaches for distinguishing adenocarcinoma from granuloma are sub-optimal.

BRIEF DESCRIPTION OF THE DRAWINGS

The accompanying drawings, which are incorporated in and constitute a part of the specification, illustrate various example apparatus, methods, and other example embodiments of various aspects of the invention. It will be appreciated that the illustrated element boundaries (e.g., boxes, groups of boxes, or other shapes) in the figures represent one example of the boundaries. One of ordinary skill in the art will appreciate that, in some examples, one element may be designed as multiple elements or that multiple elements may be designed as one element. In some examples, an element shown as an internal component of another element may be implemented as an external component and vice versa. Furthermore, elements may not be drawn to scale.

DETAILED DESCRIPTION

Figure 1:
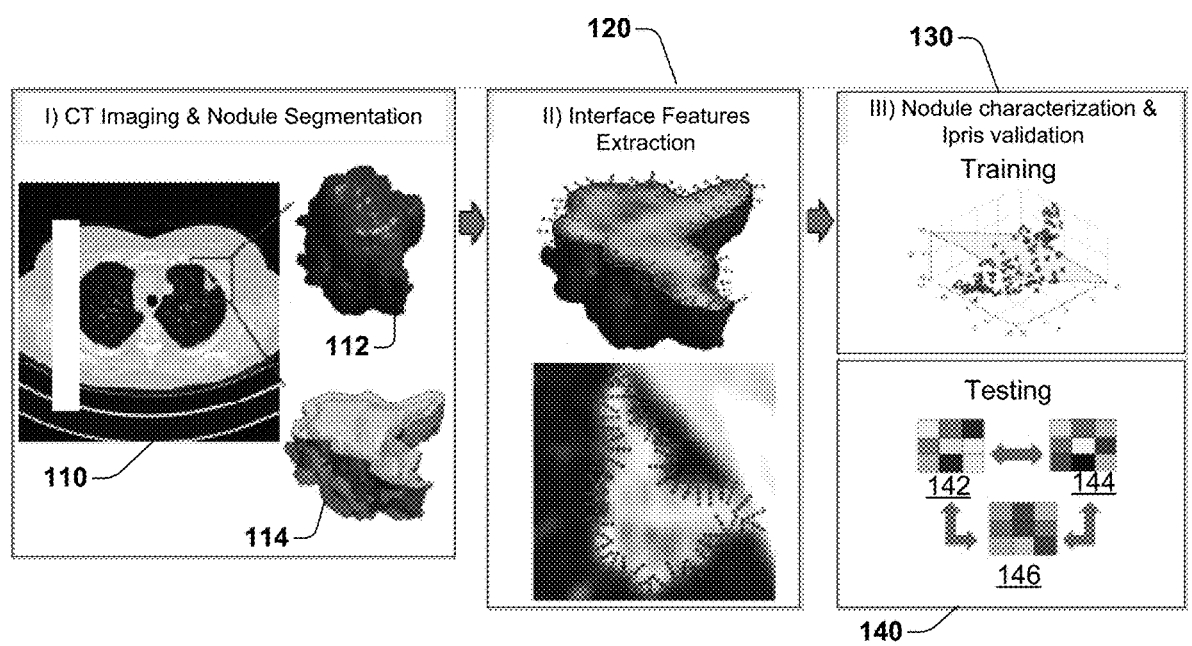
FIG. 1 is a schematic overview of an exemplary workflow for classifying lung nodules on CT imagery.

Example methods and apparatus employ intra-perinodular textural transition (Ipris), a radiomic approach, to automatically distinguish between benign and malignant nodules on routine lung computed tomography (CT) scans. Ipris represents a minimal set of quantitative measurements which capture the transition in textural appearance going from the inside to the outside of the nodule. Example embodiments partition the three dimensional (3D) volume and interface of the nodule into K nested shells, where K is an integer. Then, in one embodiment, a set of 48 Ipris features from two dimensional (2D) slices of the shells are extracted. The features pertain to the spiculations, intensity and gradient sharpness obtained from intensity differences between inner and outer voxels of an interface voxel. The Ipris features are used to train a support vector machine (SVM) classifier to distinguish between benign (granulomas) from malignant (adenocarcinomas) nodules on non-contrast CT scans. One embodiment used CT scans of 290 patients from multiple institutions, one cohort for training (N=145) and the other (N=145) for independent validation. In this embodiment, independent validation of the Ipris approach yielded an AUC of 0.83 whereas, the established conventional textural and shape radiomic features yielded a corresponding AUC of 0.75, while the AUCs for two human experts (1 pulmonologist, 1 radiologist) yielded corresponding AUCs of 0.69 and 0.73.

Embodiments described herein facilitate distinguishing benign from malignant nodules by interrogating not just the margin transition, but the textural patterns as they change from within the core of the nodule all the way to outside to nodule, and provide for a more comprehensive portrait of the heterogeneity within the nodule than existing approaches. Hence by quantitatively capturing the textural attributes from the interior through to the exterior of the nodule, embodiments described herein distinguish malignant from benign lung nodules.

Embodiments described herein employ Ipris to automatically distinguish between benign and malignant nodules on routine lung CT scans. Ipris represents a minimal set of quantitative measurements which capture the transitional heterogeneity from the intra-nodular to the peri-nodular space. The peri-nodular space, or peri-nodular zone, may include a region that includes a volume outside the boundary of the nodule. For example, a peri-nodular zone may extend 3 mm outside a tumor boundary, 6 mm, 9 mm, or other distance outside the tumor or nodule boundary. In one embodiment, computing Ipris includes segmentation of the nodule volume across contiguous slices. Then, the 3D interface of the nodule is partitioned automatically into K nested shells using morphological operations. Next, a set of 48 Ipris features from 2D slices of the shells are extracted. In one embodiment, the most predictive Ipris features are then identified using feature selection and used to train an SVM classifier in order to distinguish between benign and malignant nodules.

Embodiments characterize lung nodules represented in CT imagery by quantitatively capturing and evaluating the role of transitional heterogeneity from the intra-nodular space to the peri-nodular space to discriminate between granulomas (benign) and malignant nodules (i.e., adenocarcinoma) on lung CT images. Unlike existing approaches directed at capturing descriptors of margin sharpness, example embodiments are not limited to evaluating heterogeneity patterns solely at the nodule surface. Ipris is a 3D feature that captures the intensity and gradient transitions as well as a minimal set of textural speculation related statistics, from the inner core of the lesion all the way to the peri-nodular space. Embodiments partition the internal volume of the nodule into annular, nested shells to systematically capture heterogeneity, irregularities, and differences in growth patterns between malignant and benign nodules.

The robustness of Ipris may be demonstrated by independent validation in which it is ensured that the training and testing sets include cases from multiple different sites. Additionally, Ipris may be evaluated on CT scans with slice thicknesses that varies from 1 to 5 mm. For example, an evaluation of embodiments on a cohort of 290 patients divided randomly into training and testing sets, with extensive human-machine comparison studies involving two different human readers, was performed. Additionally, embodiments were quantitatively compared on the test set against the performance of the state of the art texture features for lung nodule characterization. Embodiments provide more accurate and more computationally efficient characterization of lung nodules on CT than existing approaches.

FIG. 1 illustrates an exemplary workflow of one embodiment described herein. FIG. 1 illustrates the main work flow of Ipris and includes, at 110, segmentation of a nodule represented in CT imagery. The nodule represented in the CT imagery is segmented at 110 to generate a 3D nodule 112. In this embodiment, nodule 112 is partitioned into k shells 114. FIG. 1 also illustrates, at 120, extraction of the 3D nodule 112's interface features from the k shells 114. FIG. 1 also illustrates, at 130, classification of nodules into benign and malignant categories by a classifier trained with Ipris features. Embodiments may train a machine learning classifier using the Ipris features extracted from a training set at step 120. At 140, the machine learning classifier trained on Ipris features is evaluated by comparing its performance 142 against the performance of texture based radiomic features 144 and expert human readers 146 on an independent test set, distinct from the training set used to construct the Ipris classifier.

Embodiments define a set of k shells based on a segmented shell. In one embodiment, a nodule represented in a CT image of a region of tissue is segmented using automated segmentation techniques. The nodule may be segmented using, for example, automated segmentation techniques including watershed segmentation, thresholding-based techniques, edge detection techniques, 3D active contour segmentation, or other segmentation techniques. Let $\Gamma = \{1, \ldots, H\} \times \{1, \ldots, W\} \times \{1, \ldots, D\}$ be a three-dimensional image lattice and v be the binary volume of a nodule defined as $v: \Gamma \to \{0,1\}$. Embodiments partition the nodule's volume into k shells such that $v = \{s_1, \ldots, sk\}, s_{i-1} \subset s_i$ and $U_{i=1}^k s_i = v$. An s consists of n 2D slices (i.e., layers) $s_i = \{l_1, \ldots, l_n\}$ and a 2D slice consists of j boundary pixels $l_i = \{p_1, \ldots, p_j\}$. Embodiments compute the slope of the normal at a boundary pixel $p_i = (x, y)$ using the co-ordinates of two adjacent pixels $p_{i-1} = (x_{i+1}, y_{i+1})$, $p_{i+1} = (x_{i+1}, y_{i+1})$ of it, and $m_p$ is defined as:

$$m_{p_i} = \frac{1}{\tan^{-1}\left(\frac{y_{i-1} - y_{i+1}}{x_{i-1} - x_{i+1}}\right)} \quad \text{Eq. 1}$$

Figure 2:
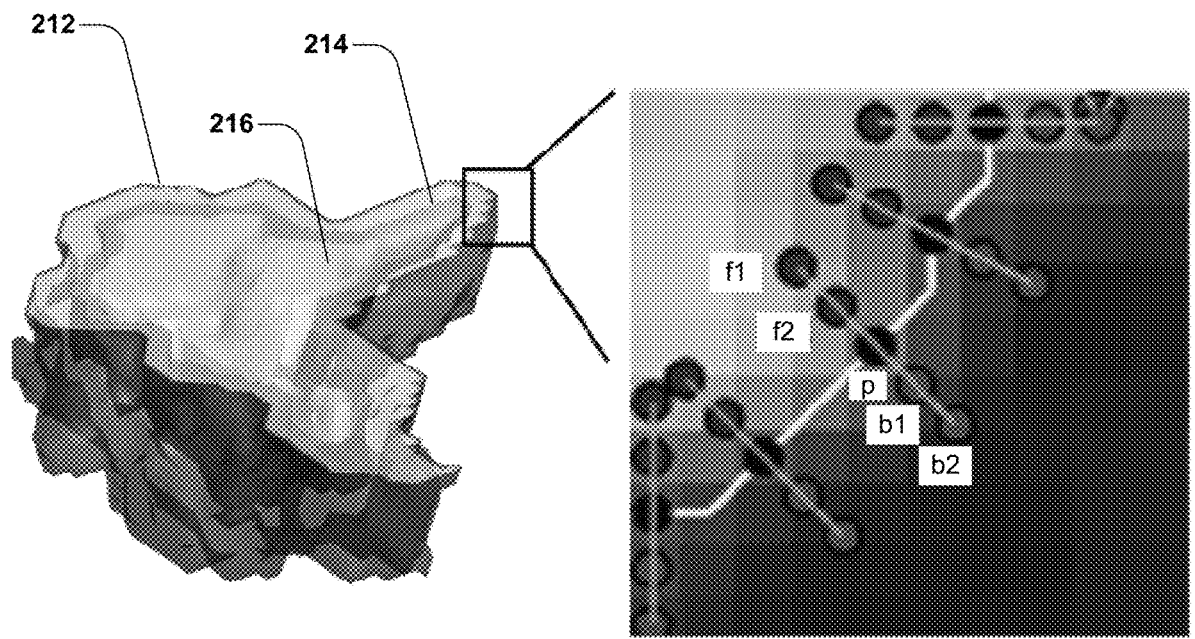
FIG. 2 illustrates shells of a lung nodule.

The normal line at a boundary pixel $p_i$ is then divided into foreground (f) and background (b) pixels. FIG. 2 illustrates, at 210, a nodule partitioned into three shells. FIG. 2 illustrates an outer shell 212, a middle shell 214, and an inner shell 216. FIG. 2 illustrates a 2D representation 220 of outer shell 212's border pixels and their corresponding normal lines including inner ($f_i$) and outer ($b_i$) pixels. Note that inner pixels extend along the normal toward the interior of the nodule, while outer pixels extend along the normal toward the outer, peri-nodular region. The normal line at a boundary pixel pi is then divided into foreground (f) and background (b) pixels. For example, pixels f1 and f2 in FIG. 2 are foreground pixels, while pixels b1 and b2 are background pixels. Foreground pixels and background pixels are located on the normal line of a boundary pixel. While three shells are illustrated in this example, embodiments may partition the nodule's volume into other, different numbers of shells. For example, the number of nested shells may depend on the size of a nodule. Thus, a first nodule having a first, larger diameter may be partitioned into six nested shells, or other, greater number of nested shells, while a second nodule having a second, smaller diameter may be partitioned into a smaller number of shells. The distance between nested shells may be based on nodule size or voxel size. For example, in one embodiment, the distance between nested shells may be based on a 2 voxels/mm ratio. In another embodiment, other distances or ratios may be employed. In one embodiment, the number of shells, or the distance between shells, may be based on available computational resources, or machine learning classifier performance.

Embodiments compute a set of Ipris features based on the shells. The average gradient difference of a $p_i$ is computed based on gradient values over f and b via:

$$dG_{p_i} = \frac{1}{Q}\Sigma_{q=1}^{Q} \frac{\nabla f_q - \nabla b_q}{2q}, \qquad \text{Eq. 2}$$

where $$Q = \frac{R}{2} - 1$$

when R is the number of pixels sampled over the normal line of pixel $p_i$ and $\nabla f_r$, $\nabla b_r$ are the gradient magnitude values of foreground and background pixels along the gradient line. Accordingly, the intensity difference profile $dI_p$ at pixel $p_i$ is calculated based on equation 4 by substituting the intensity instead of gradient values. In addition to $dG_p$, and $dI_p$, the average gradient sharpness at pixel $p_i$ is defined as:

$$dG_{p_i} = \frac{1}{R}\Sigma_{r=1}^{R} M_r, \qquad \text{Eq. 3}$$

where $M_r$ is the gradient magnitude value of the rth sample over the normal line.

Similarly, the entropy of the gradient magnitudes over the $p_i$s normal line is calculated via:

$$\varepsilon_{p_i} = \Sigma_{r=1}^{R} M_r \log_2 M_r, \qquad \text{Eq. 4}$$

Finally, for a shell s E v example embodiments calculate the mean, standard deviation, minimum, and maximum of the $dG_{p_i}$, $dI_{p_i}$, $aG_{p_i}$, and $\varepsilon_{p_i}$, according to the constituent border pixels p∈l of the 2D slices l∈s of a shell. These features are then provided to a machine learning classifier to classify the region of tissue as benign or malignant.

Embodiments may train the machine learning classifier. One embodiment employed CT scans of 290 patients acquired from multiple institutions. The data set of 290 patients divided randomly into training set $D_{train}$ and testing set $D_{test}$. One cohort $D_{train}$ is used for training (N=145) and the other $D_{test}$ (N=145) is used for independent validation. Both of the cohorts $D_{train}$ and $D_{test}$ consisted of 73 malignant and 72 benign nodules. All patients had previously undergone surgical wedge resection for a suspicious nodule and had a histopathologically confirmed diagnosis for having a malignant or benign nodule. The number of slices per scan ranged from 126 to 385, and slice thickness of the CT scans ranged from 1-6 mm. In embodiments described herein, a slice may have a thickness of at least 1 mm, a slice thickness of 6 mm, or other thickness ranging from 1 mm to 6 mm. A slice had a XY planar resolution of 512×512 pixels with a 16 bit gray scale resolution in Hounsfield Units (HU). In one embodiment, the volume of interest containing the nodules was manually segmented across contiguous slices by an expert cardiothoracic radiologist with 20 years of experience in interpreting chest CT scans, via a hand-annotation tool in 3D-Slicer software. In another embodiment, the volume of interest containing the nodules may be automatically segmented.

In one embodiment, the most informative Ipris features are selected and ranked using a Minimum Redundancy, Maximum Relevance (mRMR) feature selection approach. In this embodiment, the three most informative features were found to be (1) gray profile of the second shell ($dI_{s2}$), (2) entropy of the gradient magnitudes of the outer shell ($\varepsilon_{s1}$) and (3) the mean gradient sharpness of the outer shell ($aG_{s1}$). Note that the most informative feature in this embodiment corresponds to the second outer shell. In another embodiment, the most informative feature may correspond to another, different shell.

In one embodiment, the top ranked Ipris features are used to train an SVM classifier to distinguish benign from malignant nodules on non-contrast CT scans. To ensure a completely independent validation, embodiments train the SVM classifier using data from the $D_{train}$ set and validate the classifier using the $D_{test}$ set. The linear kernel is empirically determined for training the SVM using $D_{train}$. In one embodiment, the SVM classifier yields an AUC=0.83 in conjunction with the top ranked Ipris features on the independent validation set (n=145 scans). While in this example, an SVM classifier is trained and used to classify nodules, in another embodiment, other types of machine learning or deep learning classifiers may be employed. For example, a linear discriminant analysis (LDA) classifier, a quadratic discriminant analysis (QDA) classifier, a random forests (RF) classifier, or convolutional neural network (CNN) may be employed.

Embodiments improve on existing approaches to classifying lung nodules on CT. An embodiment using an Ipris based classifier $C_{Ipris}$ was compared with a classifier trained with existing textural and shape radiomic features $C_{rad}$. In this regard, a total of 669 radiomic features including 645 two-dimensional (2D) texture and intensity features along with 24 3D shape features were extracted from the volume of interest (i.e., nodule area). The texture features consisted of local binary pattern, gradient, Gabor filter, Laws-Laplacian pyramids, Laws and Haralick features. The shape features include some of the geometrical properties of the nodules such as size, compactness, eccentricity, elongation, convexity and sphericity. Other features may be employed.

While $C_{Ipris}$ yielded an AUC of 0.83 on the validation set, $C_{rad}$ yielded a corresponding AUC of only 0.75. Moreover, the mean Ipris feature extraction run time per one scan was 0.7 s, while it was 1.2 s for the radiomic features. Thus, not only do embodiments described herein improve the performance of a lung nodule classifier compared to existing approaches by improving the accuracy with which lung nodules are classified, but they also improve the performance of the classifier by reducing computational complexity and decreasing the time required to make a more accurate classification. Embodiments outperform existing shape and textural features from both the perspective of AUC and computational efficiency on the validation set. Additionally, in several cases using existing classification approaches, shape and texture radiomics fail to correctly discriminate the nodules owing to overlapping shape and textural appearance. In contrast, embodiments described herein more accurately differentiate benign from malignant nodules in these cases.

Figure 3:
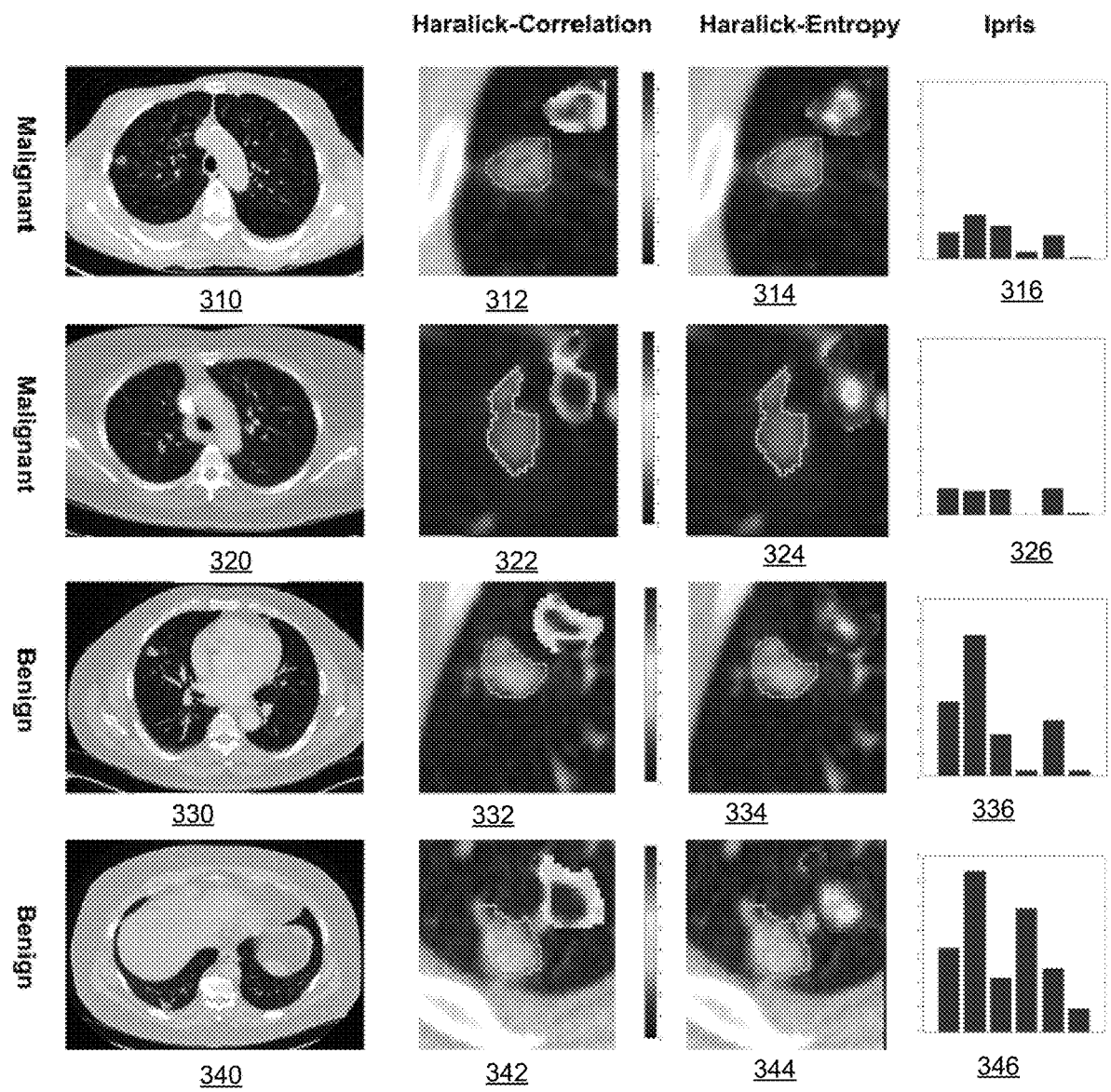
FIG. 3 illustrates texture features of malignant and benign lung nodules.

As an example of how embodiments improve on existing approaches to classifying lung nodules, FIG. 3 illustrates 4 different CT scans 310, 320, 330, and 340. CT scans 310 and 320 illustrate malignant nodules, and CT scans 330 and 340 illustrate benign nodules. Corresponding textural feature maps of Haralick correlation are illustrated at 312, 322, 332, and 342. Feature maps 312 and 322 correspond to malignant nodules illustrated in CT scans 310 and 320. Feature maps 332 and 342 correspond with benign nodules illustrated in CT scans 330 and 340. Entropy features are illustrated in feature maps 314, 324, 334, and 344. Feature maps 314 and 324 correspond to malignant nodules illustrated in CT scans 310 and 320. Feature maps 334 and 344 correspond with benign nodules illustrated in CT scans 330 and 340. The corresponding Ipris feature vectors are shown in the form of a bar plot at 316, 326, 336, and 346. Note that, the height of each column of the bar plots is a reflection of the Ipris feature value. As may be appreciable from bar plots bar 316, 326, 336, and 346, unlike the texture maps 312, 322, 332, and 342, and 314, 324, 334, and 344, which appear almost identical for both nodules, Ipris significantly over-expresses for the benign nodule and largely under-expresses for the malignant nodule.

Embodiments demonstrate improved classification accuracy compared with human performance. For example, in one embodiment, the classification performance of $C_{Ipris}$ was compared against the diagnosis of two human experts. A board certified attending radiologist with seven years of experience in thoracic radiology and a pulmonologist with seven years of experience in reading chest CT scans served as Readers 1 and 2 respectively. Both readers were blinded to the true histopathologic diagnosis of the validation set. Each reader was asked to assign a score between 1 to 5 to each nodule with 1 referring to a diagnosis of to "benign" 2 referring "mostly benign", 3 being "not sure", 4 being "mostly malignant" and 5 being "malignant". AUC values were computed based on a hard decision using a threshold of >3 and >0:5 respectively for the human readers and the machine classifier. CT based diagnosis of the two human readers including on the validation set were found to be 0.69 and 0.73 respectively. Embodiments, including $C_{Ipris}$ outperformed both human readers, having an AUC of 0.83 on the test set. Example methods and apparatus thus measurably improve on conventional approaches.

In summary, example methods and apparatus employ Ipris to automatically distinguish between benign and malignant nodules on routine lung CT scans. Ipris captures the transitional heterogeneity from the intra-nodular to the peri-nodular space and exploits the fact that the transitional patterns across the intra-nodular to the peri-nodular space may be substantially different between benign and malignant nodules on CT scans. On an independent validation set, Ipris was compared against well established existing radiomic feature approaches, and against the interpretations of two human readers. Ipris yielded a better performance compared to established existing radiomic feature approaches in terms of both classification AUC and computational efficiency. Significantly, Ipris also was found to perform substantially better compared to two human expert readers, a pulmonologist and a thoracic radiologist with seven years of experience reading chest CT scans. Additionally, Ipris is robust to the slice thickness of the CT scans, since the datasets employed in embodiments described herein involve 1-5 mm slice thickness.

Some portions of the detailed descriptions that follow are presented in terms of algorithms and symbolic representations of operations on data bits within a memory. These algorithmic descriptions and representations are used by those skilled in the art to convey the substance of their work to others. An algorithm, here and generally, is conceived to be a sequence of operations that produce a result. The operations may include physical manipulations of physical quantities. Usually, though not necessarily, the physical quantities take the form of electrical or magnetic signals capable of being stored, transferred, combined, compared, and otherwise manipulated in a logic, and so on. The physical manipulations create a concrete, tangible, useful, real-world result.

It has proven convenient at times, principally for reasons of common usage, to refer to these signals as bits, values, elements, symbols, characters, terms, numbers, and so on. It should be borne in mind, however, that these and similar terms are to be associated with the appropriate physical quantities and are merely convenient labels applied to these quantities. Unless specifically stated otherwise, it is appreciated that throughout the description, terms including processing, computing, calculating, determining, and so on, refer to actions and processes of a computer system, logic, circuit, processor, or similar electronic device that manipulates and transforms data represented as physical (electronic) quantities.

Example methods and operations may be better appreciated with reference to flow diagrams. While for purposes of simplicity of explanation, the illustrated methodologies are shown and described as a series of blocks, it is to be appreciated that the methodologies are not limited by the order of the blocks, as some blocks can occur in different orders and/or concurrently with other blocks from that shown and described. Moreover, less than all the illustrated blocks may be required to implement an example methodology. Blocks may be combined or separated into multiple components. Furthermore, additional and/or alternative methodologies can employ additional, not illustrated blocks.

Figure 4:
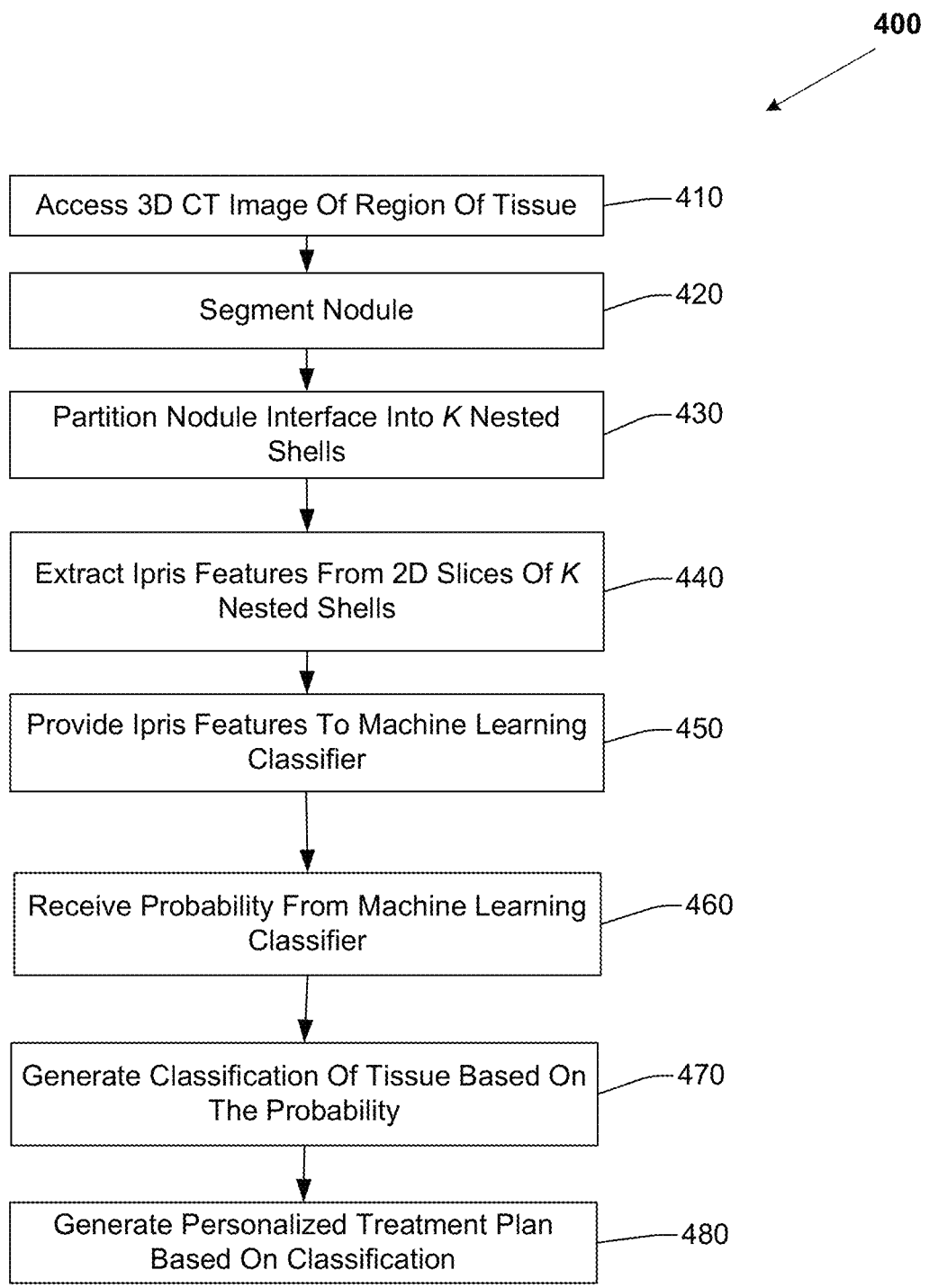
FIG. 4 is a flow diagram of example operations for classifying lung nodules on CT imagery.

FIG. 4 is a flow diagram of example operations 400 that may be performed by a processor for classifying lung nodules represented on CT imagery. A processor(s) may include any combination of general-purpose processors and dedicated processors (e.g., graphics processors, application processors, etc.). The processors may be coupled with or may include memory or storage and may be configured to execute instructions stored in the memory or storage to enable various apparatus, applications, or operating systems to perform the operations. The memory or storage devices may include main memory, disk storage, or any suitable combination thereof. The memory or storage devices may include, but are not limited to any type of volatile or non-volatile memory such as dynamic random access memory (DRAM), static random-access memory (SRAM), erasable programmable read-only memory (EPROM), electrically erasable programmable read-only memory (EEPROM), Flash memory, or solid-state storage.

The set of operations 400 includes, at 410, accessing a set of images of a region of tissue. The region of tissue may include lung tissue. A member of the set of images includes a representation of a lung nodule present in the lung tissue. Accessing the set of images includes acquiring electronic data, reading from a computer file, receiving a computer file, reading from a computer memory, or other computerized activity. A member of the set of images has a plurality of voxels, a voxel having an intensity. In one embodiment, a member of the set of images is a three dimensional (3D) computed tomography (CT) image of a region of tissue. The image includes a plurality of voxels and a plurality of slices.

In one embodiment, the plurality of slices includes one-hundred (100) slices. In another embodiment, the plurality of slices includes four-hundred (400) slices. In another embodiment, the plurality of slices includes from between one-hundred to four-hundred slices. In another embodiment, the plurality of slices may include other, different numbers of slices.

A slice has a thickness. In one embodiment, a slice has a thickness of at least 1 mm. In another embodiment, a slice has a thickness of at most 6 mm. In one embodiment, each member of the plurality of slices has the same thickness. In another embodiment, a first member of the plurality of slices has a first thickness, and a second, different member of the plurality of slices has a second, different thickness. While in this example, two different slice thicknesses are described, in another embodiment, other, different numbers of different slice thicknesses may be employed.

A slice has a resolution. In one embodiment, a member of the plurality of slices has an XY planar resolution of 512 pixels by 512 pixels. In another embodiment, other XY planar resolutions may be employed. For example a member of the plurality of slices may have an XY planar resolution of 256 pixels by 256 pixels, 1024 pixels by 1024 pixels, or other resolution.

The set of operations 400 also includes, at 420, segmenting a nodule represented in the CT image. The nodule has a 3D volume and a 3D interface. The 3D interface includes an interface voxel. Segmenting the nodule includes segmenting the 3D volume of the nodule across contiguous slices. In one embodiment, segmenting the nodule includes segmenting the nodule using a watershed technique, or may be segmented using another, different technique. For example, the nodule may be segmented manually, or the cell may be segmented using a convolutional neural network approach, or a region growing approach. In other embodiments, other segmentation techniques, including deep learning techniques may be employed.

The set of operations 400 also includes, at 430, partitioning the 3D interface of the nodule into K nested shells. K is an integer. A nested shell includes an interface. A nested shell includes a plurality of two-dimensional (2D) slices. A 2D slice includes a boundary pixel. In one embodiment, K=3. For example, a nodule may be partitioned into three shells: an outer shell, a middle shell, and an inner shell. In another embodiment, the nodule may be partitioned into other, different numbers of shells. In one embodiment, the number of nested shells is based, at least in part, on the size of the nodule. For example, a first nodule with a first volume may be partitioned into three shells, while a second nodule with a second, larger volume, may be partitioned into four, five, or six nested shells. In another embodiment, the number of nested shells may be based on another, different property of the nodule.

The set of operations 400 also includes, at 440, extracting a set of intra-perinodular textural transition (Ipris) features from a member of the plurality of 2D slices of the K nested shells. Ipris features are extracted based, at least in part, on a boundary pixel of the member of the plurality of 2D slices. In one embodiment, Ipris features are extracted by computing a normal for each boundary pixel. Ipris features are further computed by computing texture and intensity transition features along the normal line. The texture and intensity transition features may be computed based on foreground pixels and background pixels disposed along the normal line. Gradient and intensity differences are then computed for each boundary pixel based on the texture and intensity transition features. Then, second order statistics of Ipris features are computed for the shell. The second order statistics of the Ipris features may include a mean, a standard deviation, a minimum, or a maximum of the Ipris features. In another embodiment, Ipris features are extracted by computing a normal for a threshold number of boundary pixels. For example, in one embodiment, Ipris features may be extracted from 75% of the boundary pixels, 90% of the boundary pixels, or other fraction of the boundary pixels. Similarly, gradient and intensity differences may be computed for a threshold number of boundary pixels. The set of Ipris features includes sub-visual features that cannot be perceived by the human eye or extracted by pencil and paper.

The set of operations 400 also includes, at 450, providing the set of Ipris features to a machine learning classifier. Providing the set of Ipris features to the machine learning classifier includes acquiring electronic data, reading from a computer file, receiving a computer file, reading from a computer memory, or other computerized activity. In one embodiment, the machine learning classifier is a support vector machine (SVM). In another embodiment, the machine learning classifier may be another, different type of machine learning classifier. For example, the machine learning classifier may be an LDA classifier, a QDA classifier, and RF classifier, a CNN classifier, or other type of machine or deep learning classifier.

The set of operations 400 also includes, at 460, receiving from the machine learning classifier a probability that the region of tissue as benign or malignant. The machine learning classifier computes the probability based, at least in part, on the set of Ipris features. Receiving the probability includes acquiring electronic data, reading from a computer file, receiving a computer file, reading from a computer memory, or other computerized activity.

The set of operations also includes, at 470, generating a classification of the region of tissue. Generating a classification may include classifying the region of tissue as malignant or benign. For example, in one embodiment, the region of tissue may be classified as a malignant if the machine learning classifier provides a probability greater than 0.5, while the region of tissue may be classified as a benign if the probability is less than or equal to 0.5. In another embodiment, the region of tissue may be classified as malignant if the probability has another, different value, for example 0.6, 0.75, or 0.9. In one embodiment, the classification may be based on the probability and at least one of the set of images, or the Ipris features.

The set of operations 400 further includes, at 480, controlling a personalized treatment plan system to generate a personalized treatment plan. The personalized treatment plan is based, at least in part, on the classification. In one embodiment, the personalized treatment plan is further based on the set of images, or the segmented nodule. Generating a personalized treatment plan facilitates delivering a particular treatment that will be therapeutically active to the patient, while minimizing negative or adverse effects experienced by the patient. For example, the personalized treatment plan may suggest a surgical treatment, may define an immunotherapy agent dosage or schedule, or a chemotherapy agent dosage or schedule, when the nodule is classified as malignant. For a nodule classified as benign, other treatments may be suggested.

In one embodiment, the operations 400 further include training the machine learning classifier. In this embodiment, the machine learning classifier is trained and tested using a training set of images and a testing set of images. Training the machine learning classifier may include training the machine learning classifier until a threshold level of accuracy is achieved, until a threshold time has been spent training the machine learning classifier, until a threshold amount of computational resources have been expended training the machine learning classifier, or until a user terminates training. Other training termination conditions may be employed. Training the machine learning classifier may also include determining which Ipris features are most discriminative in distinguishing malignant tissue from benign tissue.

While FIG. 4 illustrates various actions occurring in serial, it is to be appreciated that various actions illustrated in FIG. 4 could occur substantially in parallel. By way of illustration, a first process could involve segmenting a nodule, a second process could involve extracting a set of features, and a third process could involve classifying a region of interest. While three processes are described, it is to be appreciated that a greater or lesser number of processes could be employed and that lightweight processes, regular processes, threads, and other approaches could be employed.

In one example, a method may be implemented as computer executable instructions. Thus, in one example, a computer-readable storage device may store computer executable instructions that if executed by a machine (e.g., computer, processor) cause the machine to perform methods or operations described or claimed herein including methods or operations 400. While executable instructions associated with the listed methods are described as being stored on a computer-readable storage device, it is to be appreciated that executable instructions associated with other example methods described or claimed herein may also be stored on a computer-readable storage device. In different embodiments the example methods described herein may be triggered in different ways. In one embodiment, a method may be triggered manually by a user. In another example, a method may be triggered automatically.

Improved classification of nodules may produce the technical effect of improving treatment efficacy by increasing the accuracy of and decreasing the time required to treat patients demonstrating adenocarcinoma, or other forms of cancerous pathology. Treatments and resources, including expensive immunotherapy agents or chemotherapy may be more accurately tailored to patients with a likelihood of benefiting from said treatments and resources, including responding to immunotherapy or chemotherapy, so that more appropriate treatment protocols may be employed, and expensive resources are not wasted. Controlling a personalized medicine system, a CADx system, a processor, or nodule or tumor classification system based on improved, more accurate identification or classification of nodules further improves the operation of the system, processor, or apparatus, since the accuracy of the system, processor, or apparatus is increased and unnecessary operations will not be performed. Embodiments described herein, including at least apparatus 600 and 700, resolve features extracted from the set of digitized CT images at a higher order or higher level than a human can resolve in the human mind or with pencil and paper. For example, the Ipris features are not biological properties of cancerous tissue that a human eye can perceive. A tumor does not include a set of nested shells and normals, and these features cannot be stored in a human mind. Embodiments described herein use a combined order of specific rules, elements, operations, or components that render information into a specific format that is then used and applied to create desired results more accurately, more consistently, and with greater reliability than existing approaches, thereby improving the performance of the computer or system with which embodiments are implemented.

Using a more appropriately modulated treatment may lead to less aggressive therapeutics being required for a patient or may lead to avoiding or delaying a biopsy, a resection, or other invasive procedure. When patients demonstrating malignant nodules are more accurately distinguished from patients who demonstrate benign nodules, patients most at risk may receive a higher proportion of scarce resources (e.g., therapeutics, physician time and attention, hospital beds) while those less likely to benefit from the treatment, or less in need, may be spared unnecessary treatment, which in turn spares unnecessary expenditures and resource consumption. Example methods, apparatus, and other embodiments may thus have the additional effect of improving patient outcomes compared to existing approaches.

Figure 5:
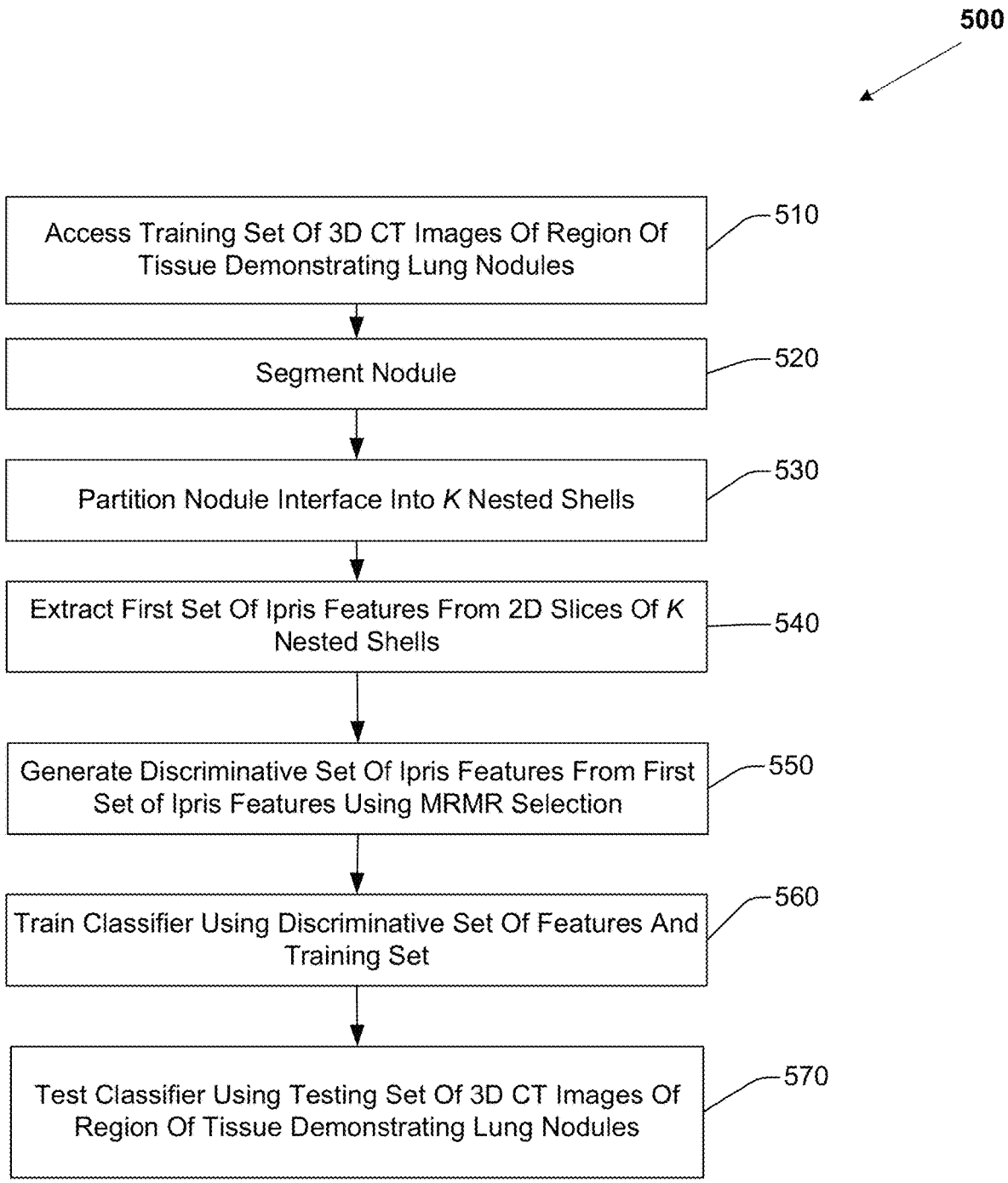
FIG. 5 illustrates is a schematic overview of an exemplary workflow for training a machine learning classifier to classify lung nodules on CT imagery.

FIG. 5 illustrates an example method 500 for training a machine learning classifier suitable for use by embodiments described herein. Method 500 includes, at 510, accessing a training set of 3D CT images of a region of tissue demonstrating lung nodules. Accessing a training set of 3D CT images includes acquiring electronic data, reading from a computer file, receiving a computer file, reading from a computer memory, or other computerized activity. A member of the training set has a plurality of voxels, a voxel having an intensity. A member of the training set has a plurality of slices.

In one embodiment, the plurality of slices includes one-hundred (100) slices. In another embodiment, the plurality of slices includes four-hundred (400) slices. In another embodiment, the plurality of slices includes from between one-hundred to four-hundred slices. In another embodiment, the plurality of slices may include other, different numbers of slices.

A slice has a thickness. In one embodiment, a slice has a thickness of 1 mm. In another embodiment, a slice has a thickness of 6 mm. In one embodiment, each member of the plurality of slices has the same thickness. In another embodiment, a first member of the plurality of slices has a first thickness, and a second, different member of the plurality of slices has a second, different thickness. While in this example, two different slice thicknesses are described, in another embodiment, other, different numbers of different slice thicknesses may be employed.

A slice has a resolution. In one embodiment, a member of the plurality of slices has an XY planar resolution of 512 pixels by 512 pixels. In another embodiment, other XY planar resolutions may be employed. For example a member of the plurality of slices may have an XY planar resolution of 256 pixels by 256 pixels, 1024 pixels by 1024 pixels, or other resolution.

Method 500 also includes, at 520, segmenting a nodule represented in a member of the training set of 3D CT images. In one embodiment, segmenting the nodule includes segmenting the nodule using a watershed technique, or may be segmented using another, different technique. For example, the nodule may be segmented manually, or the nodule may be segmented using a convolutional neural network approach, or a region growing approach. In other embodiments, other segmentation techniques, including deep learning techniques may be employed.

Method 500 also includes, at 530, partitioning the nodule interface into K nested shells. In one embodiment, K=3. In this embodiment, the 3D interface of the nodule is partitioned into a first shell, a second shell, and an outer shell. In another embodiment, the nodule interface may be partitioned into other numbers of nested shells. The number of nested shells may be based, for example, on the size of the nodule.

Method 500 also includes, at 540, extracting a first set of Ipris features from 2D slices of the K nested shells. The first set of Ipris features is extracted based, at least in part, on a boundary pixel of a member of the 2D slices. The first set of Ipris features may include, for example, 669 radiomic features including 645 2D texture features and intensity features along with 24 3D shape features extracted from the volume of interest (i.e., nodule area, perinodular region). The texture features may include local binary pattern features, gradient features, Gabor filter features, Laws-Laplacian pyramids, or Laws and Haralick features. The shape features may include geometrical properties of the nodule such as size, compactness, eccentricity, elongation, convexity or sphericity. In another embodiment, other numbers of features may be extracted.

Method 500 also includes, at 550, generating a discriminative set of Ipris features from the first set of Ipris features using an MRMR feature selection approach. The discriminative set is smaller than the first set. In one embodiment, the discriminative set of Ipris features includes a gray profile of the second shell feature, an entropy of the gradient magnitudes of the outer shell feature, and a mean gradient sharpness of the outer shell feature. In another embodiment, the discriminative set of Ipris features includes an average gradient difference feature, an intensity difference profile feature, an average gradient sharpness feature, and an entropy of gradient magnitudes feature, and a set of second order statistical features based on the average gradient difference feature, the intensity difference profile feature, the average gradient sharpness feature, and the entropy of gradient magnitudes feature.

Method 500 also includes, at 560, training a machine learning classifier using the discriminative set of Ipris features, and a training set of 3D CT images of a region of tissue demonstrating lung nodules. In one embodiment, the machine learning classifier is an SVM classifier. In another embodiment, other types of machine learning or deep learning classifiers may be trained.

Method 500 further includes, at 570, testing the machine learning classifier using a testing set of 3D CT images of a region of tissue demonstrating lung nodules. The testing set is disjoint from the training set. The testing set may be acquired using the same imaging parameters as the training set, or may be acquired using different parameters. For example, the training set may be acquired using a first slice thickness and a first resolution, while the testing set may be acquired using a second, different slice thickness and a second, different resolution. While method 500 describes acquiring CT imagery, other embodiments may employ other types of radiological imagery, including magnetic resonance imaging (MRI) imagery of a region of tissue demonstrating lung nodules, or other pathologies, including cancerous pathology, emphysema, or other lung pathologies.

Figure 6:
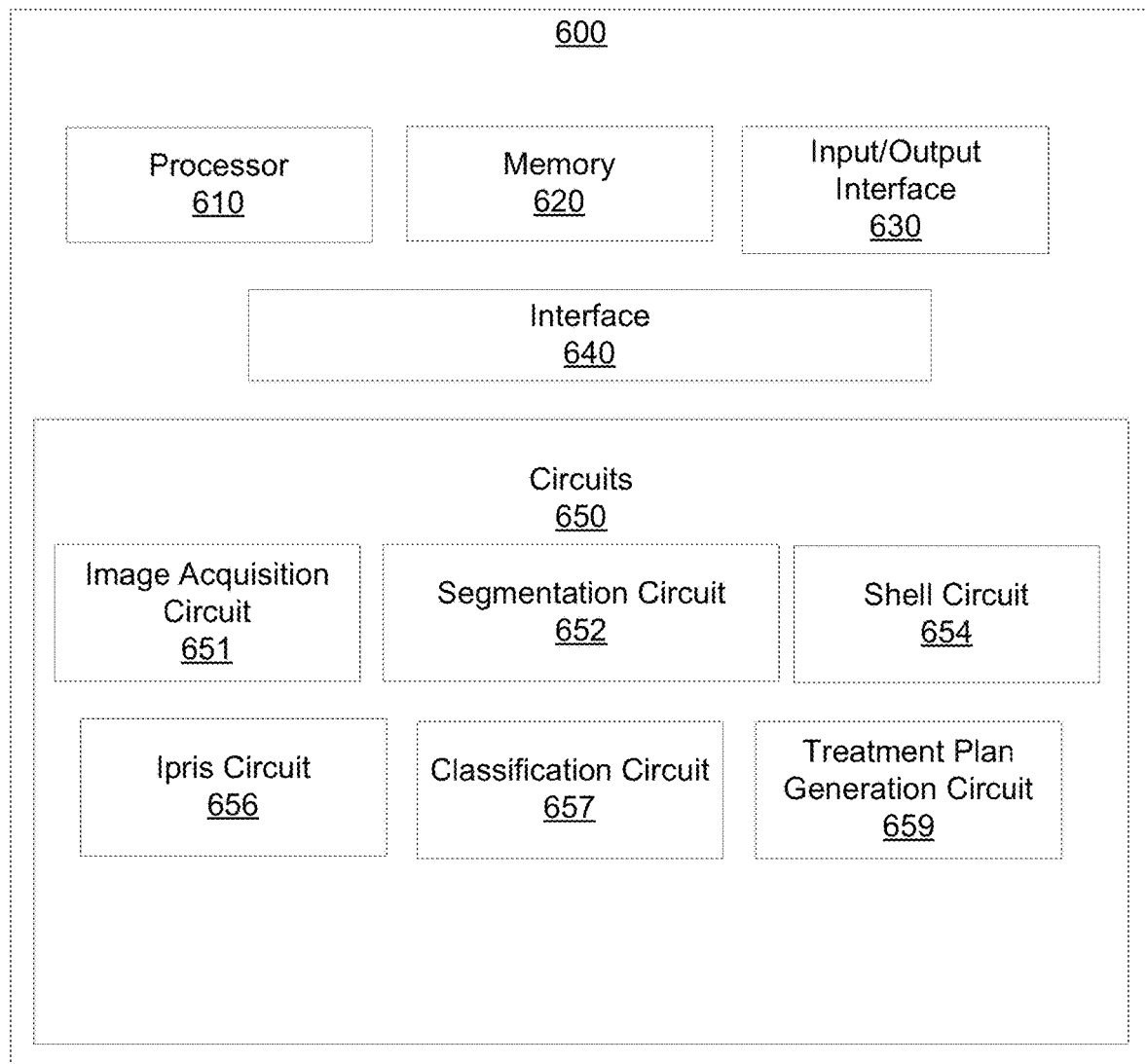
FIG. 6 illustrates an example apparatus for classifying lung nodules.

FIG. 6 illustrates an example apparatus 600 for distinguishing benign lung nodules from malignant lung nodules represented in CT imagery. Apparatus 600 includes a processor 610. Apparatus 600 also includes a memory 620. Processor 610 may, in one embodiment, include circuitry such as, but not limited to, one or more single-core or multi-core processors. Processor 610 may include any combination of general-purpose processors and dedicated processors (e.g., graphics processors, application processors, etc.). The processors may be coupled with or may include memory (e.g. memory 620) or storage and may be configured to execute instructions stored in the memory or storage to enable various apparatus, applications, or operating systems to perform the operations. Memory 620 is configured to store a set of digitized 3D images of a region of interest (ROI) demonstrating a lung nodule. A member of the set of digitized 3D images has a plurality of voxels, a voxel having an intensity. A member of the set of digitized 3D images has a plurality of slices.

Apparatus 600 also includes an input/output (I/O) interface 630, a set of circuits 650, and an interface 640 that connects the processor 610, the memory 620, the I/O interface 630, and the set of circuits 650. I/O interface 630 may be configured to transfer data between memory 620, processor 610, circuits 650, and external devices, for example, a computer assisted diagnosis (CADx) system or a personalized medicine system.

The set of circuits 650 includes an image acquisition circuit 651, a segmentation circuit 652, a shell circuit 654, an intra-perinodular textural transition (Ipris) circuit 656, and a classification circuit 657. In one embodiment, the set of circuits further includes a treatment plan generation circuit 659.

Image acquisition circuit 651 is configured to access a member of the set of digitized 3D images. A member of the set of digitized 3D images is a 3D CT image. The plurality of slices includes at least one-hundred slices. In one embodiment, the plurality of slices includes from one-hundred (100) to four-hundred (400) slices. A member of the plurality of slices has a slice thickness of 1 mm to 6 mm. In one embodiment, a first member of the plurality of slices has a first thickness, and a second, different member of the plurality of slices has a second, different thickness. In another embodiment, members of the plurality of slices may have other, different numbers of different slice thicknesses.

Segmentation circuit 652 is configured to segment a nodule represented in the CT image across contiguous slices. The nodule has a 3D volume and a 3D interface. The 3D interface of the nodule includes an interface voxel. A voxel has an intensity. In one embodiment, segmentation circuit 652 is configured to segment the nodule using a watershed technique, or may be configured to segment the nodule using another, different technique. For example, segmentation circuit 652 may be configured to segment the nodule using a convolutional neural network approach, or a region growing approach. In other embodiments, segmentation circuit 652 may be configured to employ other segmentation techniques, including deep learning techniques.

Shell circuit 654 is configured to partition the 3D interface of the nodule into K nested shells. K is an integer greater than one. A nested shell includes a plurality of 2D slices. A 2D slice includes a boundary pixel. A pixel has an intensity. In one embodiment, K=3. In this embodiment, shell circuit 654 partitions the 3D interface of the nodule into a first shell, a second shell, and an outer shell. In another embodiment, shell circuit 654 is configured to partition the 3D interface into other, different numbers of nested shells. Shell circuit 654 may be configured to partition the 3D interface into a number of shells based on a property of the nodule, including the volume of the nodule.

Ipris circuit 656 is configured to extract a set of features from a member of the plurality of 2D slices. Ipris circuit 656 extracts the set of features based, at least in part, on a normal computed from a boundary pixel of the member of the plurality of 2D slices. In one embodiment, the set of features includes a gray profile of the second shell feature, an entropy of the gradient magnitudes of the outer shell feature, and a mean gradient sharpness of the outer shell feature.

In another embodiment, the set of features includes an average gradient difference feature, an intensity difference profile feature, an average gradient sharpness feature, and an entropy of gradient magnitudes feature. In this embodiment, the set of features further includes a set of second order statistical features based on the average gradient difference feature, the intensity difference profile feature, the average gradient sharpness feature, and the entropy of gradient magnitudes feature. The set of second order statistical features may include a mean, a standard deviation, a minimum, or a maximum of members of the set of features. In another embodiment, other second order statistical features may be computed.

Classification circuit 657 is configured to compute a probability that the region of tissue is malignant. Classification circuit 657 computes the probability based, at least in part, on the set of features. Classification circuit 657 is further configured to generate a classification of the nodule as malignant or benign based, at least in part, on the probability. In one embodiment, classification circuit 657 includes a machine learning classifier configured to compute the probability based, at least in part, on the set of features using an SVM machine learning approach. In another embodiment, classification circuit 657 may be configured as another type of machine learning or deep learning classifier, including as an LDA classifier, a QDA classifier, an RF classifier, or a CNN classifier.

Treatment plan generation circuit 659 is configured to generate a personalized treatment plan based, at least in part, on the classification. In one embodiment, the personalized treatment plan is further based on the set of images, or the segmented nodule. The personalized treatment plan may suggest a surgical treatment, may define an immunotherapy agent dosage or schedule, or a chemotherapy agent dosage or schedule, when the nodule is classified as malignant. For a nodule classified as benign, other treatments may be suggested.

Figure 7:
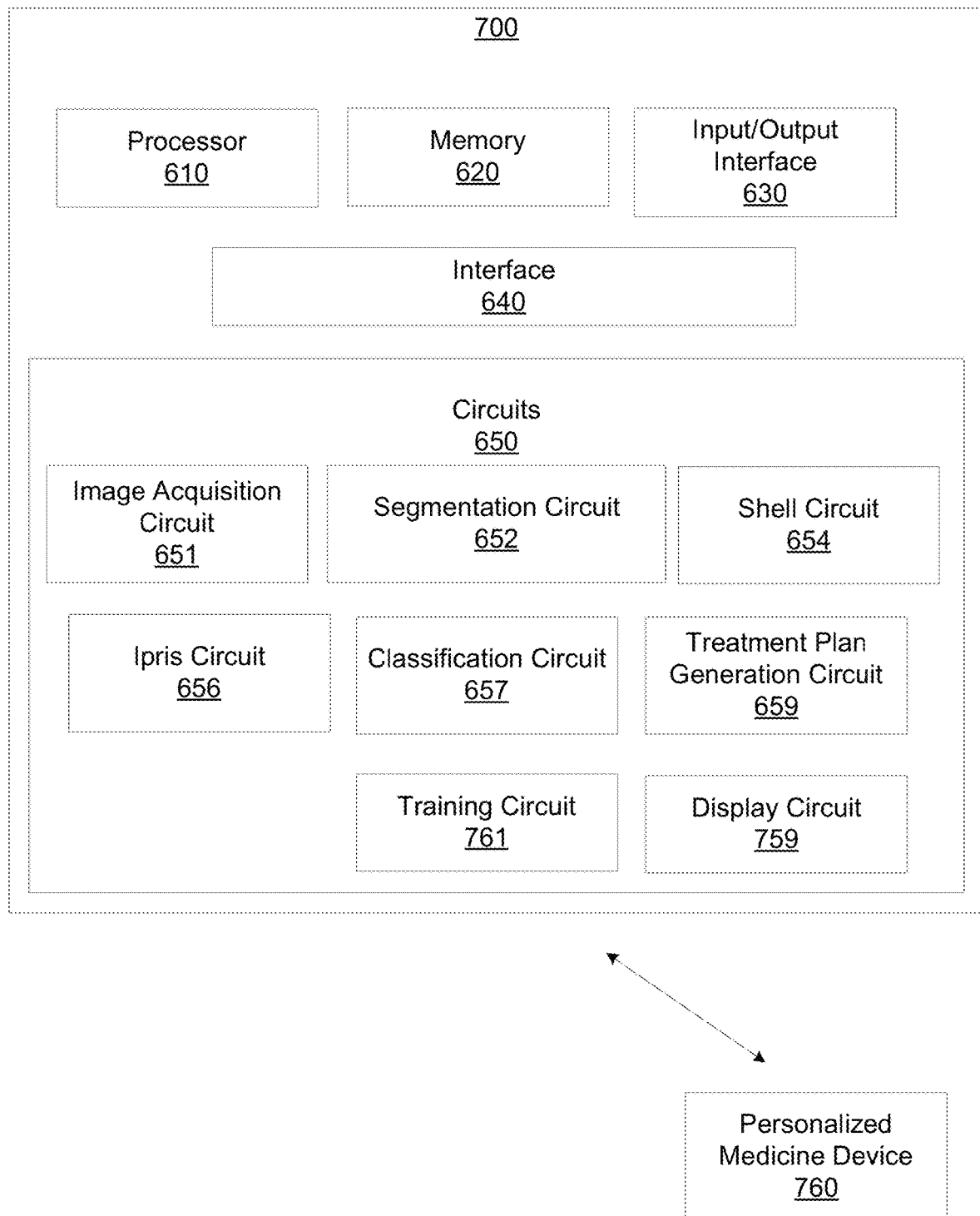
FIG. 7 illustrates an example apparatus for classifying lung nodules.

FIG. 7 illustrates an apparatus 700 that is similar to apparatus 600 but that includes additional elements and details. Apparatus 700 includes a display circuit 759. Display circuit 759 is configured to display the classification, the probability, the personalized treatment plan, the set of features, or the member of the set of digitized 3D images. In one embodiment, display circuit 759 is configured to display the classification, the probability, the personalized treatment plan, the set of features, or the member of the set of digitized 3D images on a computer monitor, a smartphone display, a tablet display, or other displays. Displaying the classification, the probability, the personalized treatment plan, the set of features, or the member of the set of digitized 3D images may also include printing the classification, the probability, the personalized treatment plan, the set of features, or the member of the set of digitized 3D images. Display circuit 759 may also control a CADx system, a monitor, or other display, to display operating parameters or characteristics of image acquisition circuit 651, segmentation circuit 652, shell circuit 654, Ipris circuit 656, or classification circuit 657, including a machine learning classifier, during both training and testing, or during clinical operation of apparatus 600 or apparatus 700.

In one embodiment, apparatus 700 also includes training circuit 761. Training circuit 761 is configured to train classification circuit 657 according to techniques described herein, including method 500. Training classification circuit 657 may include training a machine learning classifier. In one embodiment, training circuit 761 is configured to access a dataset of digitized images of a region of interest demonstrating lung nodules. In this embodiment, the machine learning classifier is trained and tested using a training set of images and a testing set of images. Training the machine learning classifier may include training the machine learning classifier until a threshold level of accuracy is achieved, until a threshold time has been spent training the machine learning classifier, until a threshold amount of computational resources have been expended training the machine learning classifier, or until a user terminates training. Other training termination conditions may be employed.

FIG. 7 further illustrates a personalized medicine device 760. Apparatus 700 may be configured to transmit the classification, the probability, the personalized treatment plan, the set of features, or the member of the set of digitized 3D images to the personalized medicine device 760. Personalized medicine device 760 may be, for example, a CADx system, a nodule classification system, or other type of personalized medicine device that may be used to facilitate the classification of tissue. In one embodiment, treatment plan generation circuit 659 may control personalized medicine device 760 to display the classification, the probability, the personalized treatment plan, the set of features, or the member of the set of digitized 3D images on a computer monitor, a smartphone display, a tablet display, or other displays.

Figure 8:
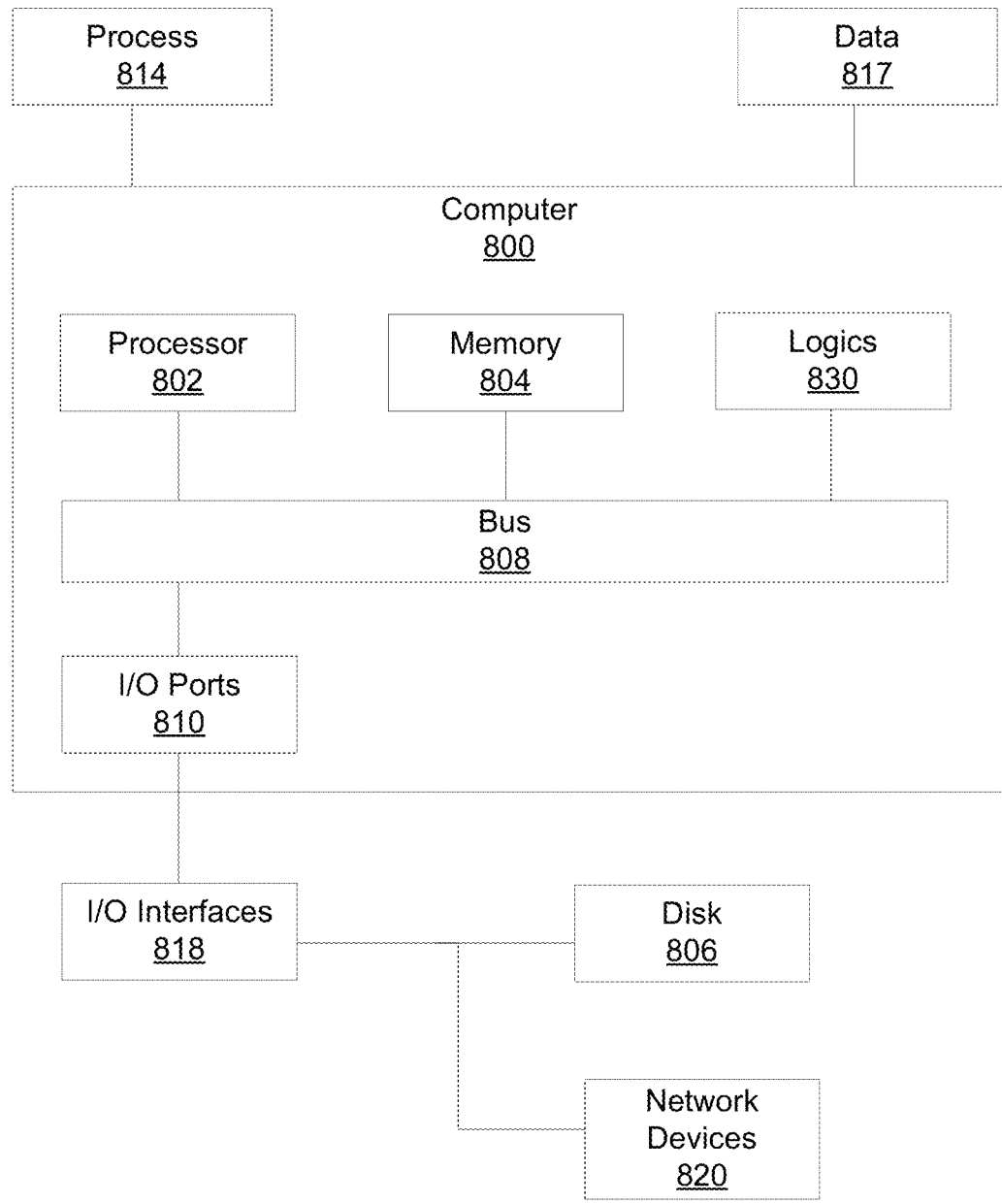
FIG. 8 illustrates an example computer in which embodiments described herein may operate.

FIG. 8 illustrates an example computer 800 in which example methods illustrated herein can operate and in which example methods, apparatus, circuits, operations, or logics may be implemented. In different examples, computer 800 may be part of a personalized medicine system, a nodule or tumor classification system, an MRI system, a digital whole slide scanner, a CT system, may be operably connectable to a CT system, an MRI system, a personalized medicine system, or a digital whole slide scanner, or may be part of a CADx system.

Computer 800 includes a processor 802, a memory 804, and input/output (I/O) ports 810 operably connected by a bus 808. In one example, computer 800 may include a set of logics or circuits 830 that perform a method of classifying lung nodules using a machine learning classifier. Thus, the set of circuits 830, whether implemented in computer 800 as hardware, firmware, software, and/or a combination thereof may provide means (e.g., hardware, firmware, circuits) for characterizing intra-tumoral heterogeneity, or characterizing a nodule or tumor as malignant or benign. In different examples, the set of circuits 830 may be permanently and/or removably attached to computer 800.

Processor 802 can be a variety of various processors including dual microprocessor and other multi-processor architectures. Processor 802 may be configured to perform steps of methods claimed and described herein. Memory 804 can include volatile memory and/or non-volatile memory. A disk 806 may be operably connected to computer 800 via, for example, an input/output interface (e.g., card, device) 818 and an input/output port 810. Disk 806 may include, but is not limited to, devices like a magnetic disk drive, a tape drive, a Zip drive, a flash memory card, or a memory stick. Furthermore, disk 806 may include optical drives like a CD-ROM or a digital video ROM drive (DVD ROM). Memory 804 can store processes 814 or data 817, for example. Data 817 may, in one embodiment, include digitized CT images of a region of lung tissue demonstrating nodules. Disk 806 or memory 804 can store an operating system that controls and allocates resources of computer 800.

Bus 808 can be a single internal bus interconnect architecture or other bus or mesh architectures. While a single bus is illustrated, it is to be appreciated that computer 800 may communicate with various devices, circuits, logics, and peripherals using other buses that are not illustrated (e.g., PCIE, SATA, Infiniband, 794, USB, Ethernet).

Computer 800 may interact with input/output devices via I/O interfaces 818 and input/output ports 810. Input/output devices can include, but are not limited to, CT systems, MRI systems, digital whole slide scanners, an optical microscope, a keyboard, a microphone, a pointing and selection device, cameras, video cards, displays, disk 806, network devices 820, or other devices. Input/output ports 810 can include but are not limited to, serial ports, parallel ports, or USB ports.

Computer 800 may operate in a network environment and thus may be connected to network devices 820 via I/O interfaces 818 or I/O ports 810. Through the network devices 820, computer 800 may interact with a network. Through the network, computer 800 may be logically connected to remote computers. The networks with which computer 800 may interact include, but are not limited to, a local area network (LAN), a wide area network (WAN), or other networks, including the cloud.

Figure 9:
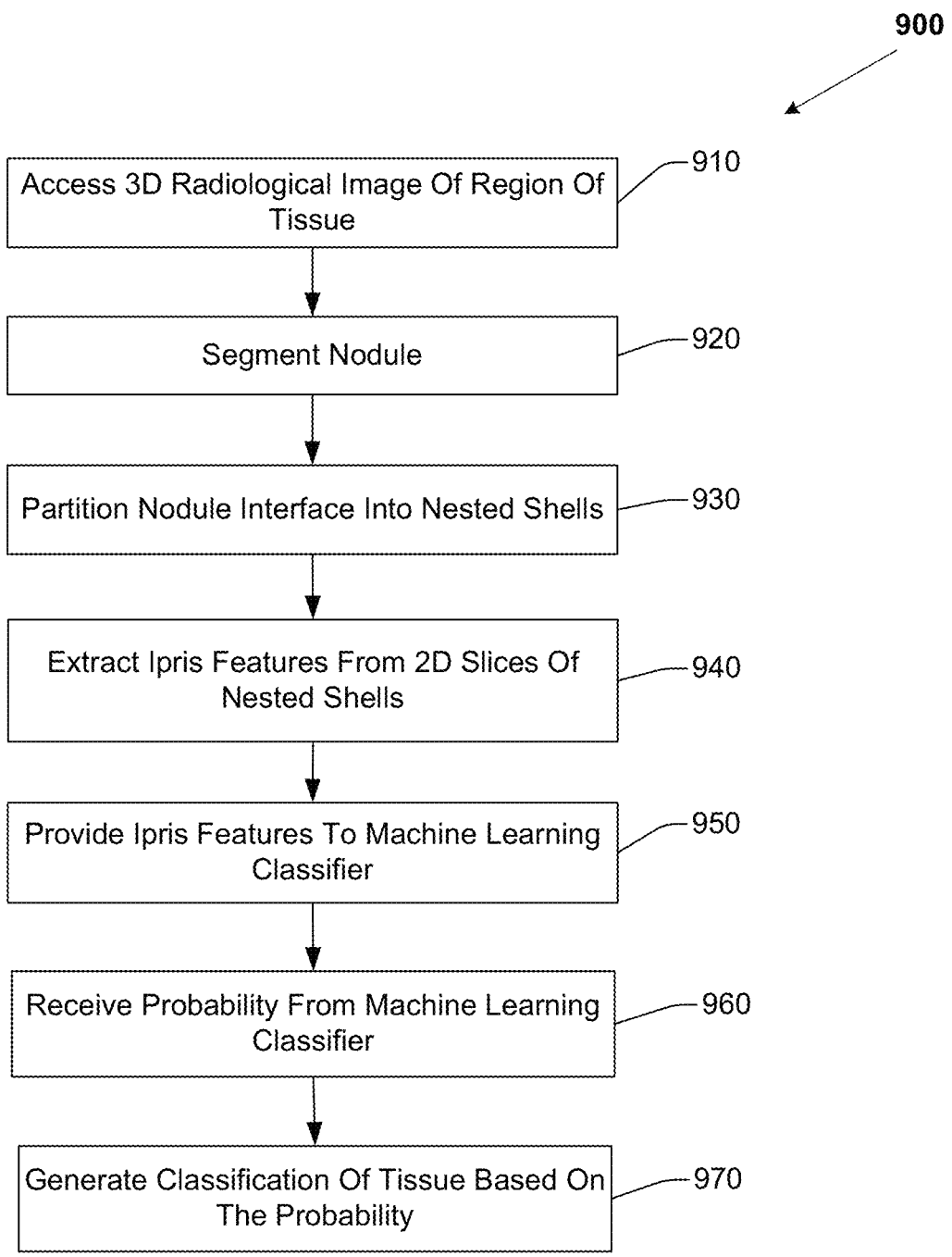
FIG. 9 illustrates an example method for classifying lung nodules represented in radiological imagery.

FIG. 9 illustrates an example method 900 for classifying a nodule represented in a radiological image. Method 900 includes, at 910, accessing a 3D radiological image of a region of tissue. The region of tissue includes a nodule. The 3D radiological image includes a plurality of voxels and a plurality of slices. A voxel has an intensity. A slice has a thickness. In one embodiment, a first member of the plurality of slices has a first thickness, and a second, different member of the plurality of slices has a second, different thickness.

Method 900 also includes, at 920, segmenting the nodule represented in the 3D radiological image across contiguous slices. The nodule has a 3D volume and a 3D interface. The 3D interface includes an interface voxel. Segmenting the nodule may include segmenting the nodule using a watershed technique, a convolutional neural network approach, or a region growing approach. In other embodiments, other segmentation techniques, including deep learning techniques, may be employed.

Method 900 also includes, at 930, partitioning the 3D interface of the nodule into a plurality of nested shells. A nested shell includes a plurality of 2D slices, where a 2D slice includes a boundary pixel. In one embodiment, the 3D interface of the nodule is partitioned into three nested shells. An outer shell may define a boundary between the nodule and a peri-nodular region. In another embodiment, the 3D interface of the nodule may be partitioned into other, different numbers of nested shells.

Method 900 also includes, at 940, extracting a set of intra-perinodular textural transition (Ipris) features from a member of the plurality of 2D slices. The set of Ipris features is based, at least in part, on a normal computed from a boundary pixel of the member of the plurality of 2D slices. The set of Ipris features captures transitional heterogeneity between nested shells, and from the intra-nodular region to the peri-nodular region.

Method 900 also includes, at 950, providing the set of Ipris features to a machine learning classifier. The machine learning classifier may be, in one embodiment, an SVM classifier. In another embodiment, other types of machine learning or deep learning classifiers may be employed.

Method 900 also includes, at 960, receiving, from the machine learning classifier, a probability that the nodule is malignant. The probability is computed by the machine learning classifier based, at least in part, on the set of Ipris features.

Method 900 further includes, at 970, generating a classification of the nodule based, at least in part, on the probability. The classification may classify the nodule as malignant, or as benign. In one embodiment, method 900 further includes displaying the classification, the probability, the set of Ipris features, the plurality of 2D slices, the 3D interface, the plurality of nested shells, or the radiological image.

Examples herein can include subject matter such as an apparatus, a personalized medicine system, a CADx system, a processor, a system, a method, means for performing acts, steps, or blocks of the method, at least one machine-readable medium including executable instructions that, when performed by a machine (e.g., a processor with memory, an application-specific integrated circuit (ASIC), a field programmable gate array (FPGA), or the like) cause the machine to perform acts of the method or of an apparatus or system for classifying lung nodules, according to embodiments and examples described.

References to "one embodiment", "an embodiment", "one example", and "an example" indicate that the embodiment(s) or example(s) so described may include a particular feature, structure, characteristic, property, element, or limitation, but that not every embodiment or example necessarily includes that particular feature, structure, characteristic, property, element or limitation. Furthermore, repeated use of the phrase "in one embodiment" does not necessarily refer to the same embodiment, though it may.

"Computer-readable storage device", as used herein, refers to a device that stores instructions or data. "Computer-readable storage device" does not refer to propagated signals. A computer-readable storage device may take forms, including, but not limited to, non-volatile media, and volatile media. Non-volatile media may include, for example, optical disks, magnetic disks, tapes, and other media. Volatile media may include, for example, semiconductor memories, dynamic memory, and other media. Common forms of a computer-readable storage device may include, but are not limited to, a floppy disk, a flexible disk, a hard disk, a magnetic tape, other magnetic medium, an application specific integrated circuit (ASIC), a compact disk (CD), other optical medium, a random access memory (RAM), a read only memory (ROM), a memory chip or card, a memory stick, and other media from which a computer, a processor or other electronic device can read.

"Circuit", as used herein, includes but is not limited to hardware, firmware, software in execution on a machine, or combinations of each to perform a function(s) or an action(s), or to cause a function or action from another logic, method, or system. A circuit may include a software controlled microprocessor, a discrete logic (e.g., ASIC), an analog circuit, a digital circuit, a programmed logic device, a memory device containing instructions, and other physical devices. A circuit may include one or more gates, combinations of gates, or other circuit components. Where multiple logical circuits are described, it may be possible to incorporate the multiple logical circuits into one physical circuit. Similarly, where a single logical circuit is described, it may be possible to distribute that single logical circuit between multiple physical circuits.

To the extent that the term "includes" or "including" is employed in the detailed description or the claims, it is intended to be inclusive in a manner similar to the term "comprising" as that term is interpreted when employed as a transitional word in a claim.

Throughout this specification and the claims that follow, unless the context requires otherwise, the words 'comprise' and 'include' and variations such as 'comprising' and 'including' will be understood to be terms of inclusion and not exclusion. For example, when such terms are used to refer to a stated integer or group of integers, such terms do not imply the exclusion of any other integer or group of integers.

To the extent that the term "or" is employed in the detailed description or claims (e.g., A or B) it is intended to mean "A or B or both". When the applicants intend to indicate "only A or B but not both" then the term "only A or B but not both" will be employed. Thus, use of the term "or" herein is the inclusive, and not the exclusive use. See, Bryan A. Garner, A Dictionary of Modern Legal Usage 624 (2d. Ed. 1995).

While example systems, methods, and other embodiments have been illustrated by describing examples, and while the examples have been described in considerable detail, it is not the intention of the applicants to restrict or in any way limit the scope of the appended claims to such detail. It is, of course, not possible to describe every conceivable combination of components or methodologies for purposes of describing the systems, methods, and other embodiments described herein. Therefore, the invention is not limited to the specific details, the representative apparatus, and illustrative examples shown and described. Thus, this application is intended to embrace alterations, modifications, and variations that fall within the scope of the appended claims.

What is claimed is:

1. A non-transitory computer-readable storage device storing computer executable instructions that when executed by a processor control the computer to perform operations comprising:
    accessing a three dimensional (3D) computed tomography (CT) image of a region of tissue, where the image includes a plurality of voxels and a plurality of slices, a slice having a thickness, where the region of tissue includes lung tissue;
    segmenting a nodule represented in the CT image across contiguous slices, where the nodule has a 3D volume and a 3D interface, where the 3D interface includes an interface voxel;
    partitioning the 3D interface of the nodule into K nested shells, where K is an integer, where a nested shell includes a plurality of two-dimensional (2D) slices, where a 2D slice includes a boundary pixel;
    extracting a set of intra-perinodular textural transition (Ipris) features from a member of the plurality of 2D slices of the K nested shells based, at least in part, on a normal computed from a boundary pixel of the member of the plurality of 2D slices;
    providing the set of Ipris features to a machine learning classifier;
    receiving, from the machine learning classifier, a probability that the region of tissue is malignant, based, at least in part, on the set of Ipris features;
    generating a classification of the region of tissue based, at least in part, on the probability; and
    controlling a personalized cancer therapy system to generate a personalized treatment plan based, at least in part, on the classification.

2. The non-transitory computer-readable storage device of claim 1, where the plurality of slices includes from one-hundred to four-hundred slices.

3. The non-transitory computer-readable storage device of claim 1, where a member of the plurality of slices has a slice thickness of at least 1 mm to at most 6 mm.

4. The non-transitory computer-readable storage device of claim 1, where a member of the plurality of slices has an XY planar resolution of 512 pixels by 512 pixels.

5. The non-transitory computer-readable storage device of claim 1, where K=3, and where the K nested shells includes a first shell, a second shell, and an outer shell.

6. The non-transitory computer-readable storage device of claim 5, where the set of Ipris features includes a gray profile of the second shell feature, an entropy of the gradient magnitudes of the outer shell feature, and a mean gradient sharpness of the outer shell feature.

7. The non-transitory computer-readable storage device of claim 1, where the set of Ipris features includes an average gradient difference feature, an intensity difference profile feature, an average gradient sharpness feature, and an entropy of gradient magnitudes feature, and a set of second order statistical features based on the average gradient difference feature, the intensity difference profile feature, the average gradient sharpness feature, and the entropy of gradient magnitudes feature.

8. The non-transitory computer-readable storage device of claim 1, where the machine learning classifier is a support vector machine (SVM) classifier.

9. The non-transitory computer-readable storage device of claim 1, where the machine learning classifier is a linear discriminant analysis (LDA) classifier, a quadratic discriminant analysis (QDA) classifier, a random forests (RF) classifier, or a convolutional neural network (CNN) classifier.

10. The non-transitory computer-readable storage device of claim 1, the operations further comprising displaying at least one of the classification, the probability, the set of Ipris features, the 3D CT image, or the personalized treatment plan.

11. An apparatus for distinguishing benign nodules from malignant nodules in lung computed tomography (CT) imagery, the apparatus comprising:
    a processor;
    a memory configured to store a set of digitized three dimensional (3D) images of a region of interest (ROI) demonstrating a lung nodule, where a member of the set of digitized 3D images has a plurality of voxels, a voxel having an intensity, and where a member of the set of digitized 3D images has a plurality of slices;
    an input/output (I/O) interface;
    a set of circuits comprising an image acquisition circuit, a segmentation circuit, a shell circuit, an intra-perinodular textural transition (Ipris) circuit, and a classification circuit; and
    an interface that connects the processor, the memory, the I/O interface, and the set of circuits;
    the image acquisition circuit configured to access a member of the set of digitized 3D images;
    the segmentation circuit configured to:
        segment a nodule represented in the member of the set of digitized 3D images across contiguous slices, where the nodule has a 3D volume and a 3D interface, where the 3D interface includes an interface voxel;
    the shell circuit configured to:
        partition the 3D interface of the nodule into K nested shells, where K is an integer, where a nested shell includes a plurality of two-dimensional (2D) slices, where a 2D slice includes a boundary pixel;
    the Ipris circuit configured to:
        extract a set of features from a member of the plurality of 2D slices based, at least in part, on a normal computed from a boundary pixel of the member of the plurality of 2D slices; and
    the classification circuit configured to:
        compute a probability that the ROI is malignant, based, at least in part, on the set of features; and
        generate a classification of the ROI as malignant or benign based, at least in part, on the probability.

12. The apparatus of claim 11, where a member of the set of digitized 3D images is a 3D computed tomography (CT) image, where the plurality of slices includes at least one-hundred slices, and where a member of the plurality of slices has a slice thickness of at least 1 mm to at most 6 mm.

13. The apparatus of claim 11, where K=3, and where the shell circuit partitions the 3D interface of the nodule into a first shell, a second shell, and an outer shell.

14. The apparatus of claim 13, where the set of features includes:
a gray profile of the second shell feature, an entropy of the gradient magnitudes of the outer shell feature, and a mean gradient sharpness of the outer shell feature.

15. The apparatus of claim 11, where the set of features includes an average gradient difference feature, an intensity difference profile feature, an average gradient sharpness feature, and an entropy of gradient magnitudes feature; and
a set of second order statistical features based on the average gradient difference feature, the intensity difference profile feature, the average gradient sharpness feature, and the entropy of gradient magnitudes feature.

16. The apparatus of claim 11, where the classification circuit includes a machine learning classifier configured to compute the probability based, at least in part, on the set of features using a support vector machine (SVM) machine learning approach.

17. The apparatus of claim 11, the set of circuits further comprising a treatment plan generation circuit configured to generate a personalized treatment plan based, at least in part, on the classification.

18. The apparatus of claim 17, the set of circuits further comprising a display circuit configured to display the classification, the probability, the personalized treatment plan, the set of features, or the member of the set of digitized 3D images.

* * * * *

UNITED STATES PATENT AND TRADEMARK OFFICE
CERTIFICATE OF CORRECTION

PATENT NO. : 10,692,211 B2
APPLICATION NO. : 16/012937
DATED : June 23, 2020
INVENTOR(S) : Anant Madabhushi et al.

It is certified that error appears in the above-identified patent and that said Letters Patent is hereby corrected as shown below:

In the Specification

Column 1, Lines 16 through 23; please replace "This invention was made with government support under grants 1U24CA199374-01, R01CA202752-01A1, R01CA208236-01A1, R21CA179327-01, R21CA195152-01, R01DK098503-02, and 1 C06 RR012463-01 awarded by the National Institutes of Health. Also grants W81XWH-13-1-0418, W81XWH-14-1-0323, W81XWH16-1-0329, and W81XWH-15-1-0613 awarded by the Department of Defense. The government has certain rights in the invention." with --This invention was made with government support under grants CA179327, CA195152, CA199374, CA202752, CA208236, DK098503, and RR012463 awarded by the National Institutes of Health; and grant(s) W81XWH-16-1-0329, W81XWH-14-1-0323, W81XWH-13-1-0418, and W81XWH-15-1-0613 awarded by the Department of Defense. The government has certain rights in the invention.--

Signed and Sealed this
Fourteenth Day of September, 2021

Drew Hirshfeld
*Performing the Functions and Duties of the*
*Under Secretary of Commerce for Intellectual Property and*
*Director of the United States Patent and Trademark Office*